United States Patent
Asami et al.

(10) Patent No.: US 6,958,311 B2
(45) Date of Patent: Oct. 25, 2005

(54) FLOWERING REGULATORS

(75) Inventors: Tadao Asami, Tokyo (JP); Shigeo Yoshida, Tokyo (JP)

(73) Assignee: Riken, Saitama (JP)

(*) Notice: Subject to any disclaimer, the term of this patent is extended or adjusted under 35 U.S.C. 154(b) by 0 days.

(21) Appl. No.: 10/332,993

(22) PCT Filed: Jul. 19, 2001

(86) PCT No.: PCT/JP01/06272

§ 371 (c)(1),
(2), (4) Date: Apr. 15, 2003

(87) PCT Pub. No.: WO02/09520

PCT Pub. Date: Feb. 7, 2002

(65) Prior Publication Data

US 2003/0162663 A1 Aug. 28, 2003

(30) Foreign Application Priority Data

Jul. 27, 2000 (JP) .................................... 2000-226361

(51) Int. Cl.[7] ............................................ A01N 43/653
(52) U.S. Cl. .................................................. 504/272
(58) Field of Search ....................... 504/272; 514/383; 548/262.2

(56) References Cited

U.S. PATENT DOCUMENTS

| | | | | |
|---|---|---|---|---|
| 4,162,155 A | * | 7/1979 | Young | 504/317 |
| 4,243,405 A | | 1/1981 | Balasubramanyan et al. | 71/76 |
| 4,472,415 A | | 9/1984 | Worthington et al. | 424/269 |
| 4,620,011 A | | 10/1986 | Worthington et al. | 548/262 |
| 4,690,941 A | | 9/1987 | Worthington et al. | 514/383 |
| 4,895,589 A | | 1/1990 | Elliott et al. | 71/92 |
| 4,912,121 A | | 3/1990 | Worthington et al. | 514/383 |
| 5,597,778 A | * | 1/1997 | Smale | 504/127 |
| 6,388,089 B1 | | 5/2002 | Yoshida et al. | 548/262.2 |
| 6,706,666 B2 | * | 3/2004 | Hasebe et al. | 504/365 |

FOREIGN PATENT DOCUMENTS

| | | |
|---|---|---|
| EP | 0127944 | 12/1984 |
| GB | 1529818 | 10/1978 |
| GB | 1544028 | 4/1979 |
| GB | 1595696 | 8/1981 |
| GB | 0212841 | 3/1987 |
| JP | 56-34605 | 4/1981 |
| JP | 2000-53657 | 2/2000 |
| JP | 2001-247553 | 9/2001 |
| WO | 00/09490 | * 2/2000 |

OTHER PUBLICATIONS

Min et al. "New Lead Compounds for Brassinosteroid Biosynthesis Inhibitors". Bioorganic and Medicinal Chemistry Letters. 9:425–430. Feb 8, 1999.*
Asami et al. "Characterization of Brassinazole, a Triazole-Type Brassinosteroid Biosynthesis Inhibitor". Plant Physiology. 123:93–99. May 2000.*

(Continued)

Primary Examiner—S. Mark Clardy
(74) Attorney, Agent, or Firm—Greenblum & Bernstein, P.L.C.

(57) ABSTRACT

A flowering regulator comprising a compound represented by the following formula (I):

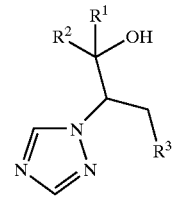

wherein $R^1$ represents a lower alkyl group, a lower alkenyl group, or a phenyl group which may be substituted, $R^2$ represents a lower alkyl group or a phenyl group which may be substituted, and $R^3$ represents a phenyl group which may be substituted (e.g., 4-(4-chlorophenyl)-2-phenyl-3-(1,2,4-triazoyl)butan-2-ol), or a salt thereof.

8 Claims, 1 Drawing Sheet

OTHER PUBLICATIONS

Asami et al. "Brassinosteroid biosynthesis inhibitors" Trends in Plant Science. 4(9):348–353. Sep. 1999.*
Yokota, T., Trends in Plant Science, 2, pp. 137–143, 1997.
Mandava, N. B., Ann. Rev. Plant Physiol. Plant Mol. Biol., 39, pp. 23–52, 1988.
Schlagnaufer, C., et al., Physiol. Plant., 61, pp. 555–558, 1984.
Iwasaki, T., et al., Plant Cell Physiol., 32, pp. 1007–1014, 1991.
Yamamoto, R., et al., Plant Cell Physiol., 38, pp. 980–983, 1997.
Azpiroz, R., et al., The Plant Cell, 10, pp. 219–230, 1998.
Clouse, S. D., The Plant Journal, 10, pp. 1–8, 1996.
Fujioka, S., et al., Physiol. Plant., 100, pp. 710–715, 1997.
Feldmann, K. A., et al., Science, 243, pp. 1351–1354, 1989.
Takahashi, T., et al., Genes & Dev., 9, pp. 97–107, 1995.
Kauschmann, A., et al., The Plant J., 9, pp. 701–713, 1996.
Szekeres M., et al., Cell, 85, pp. 171–182, 1996.
Li, J., et al., Science, 272, pp. 398–401, 1996.
Fujioka, S., et al., The Plant Cell, 9, pp. 1951–1962, 1997.
Nomura, T., et al., Plant Physiol., 113, pp. 31–37, 1997.
Yokota, T., et al., "Gibberillin", Springer Verlag, New York, pp. 339–349.
U.S. Appl. No. 10/332,994 filed Jan. 24, 2003 (National Stage of PCT/JP01/06273 filed Jul. 19, 2001) having the title "Brassinosteroid Metabolism Inhibitor" (Applicants: Tadao ASAMI et al.).

* cited by examiner

FLOWERING REGULATORS

TECHNICAL FIELD

The present invention relates to a flowering regulator.

BACKGROUND ART

Brassinosteroids have been recently recognized as a new class of plant hormones through the combination of molecular genetics and researches on biosyntheses (Yokota, Trends in Plant Sci., 2, pp. 137–143, 1997). Since the chemistry of brassinosteroids was established, biological activities of these homologues have been extensively studied, and their notable actions on plant growth have been revealed, which include elongation of stalks, growth of pollen tubes, inclination of leaves, opening of leaves, suppression of roots, activation of proton pump (Mandava and Annu. Rev. Plant Physiol. Plant Mol. Biol., 39, pp. 23–52, 1988), acceleration of ethylene production (Schlagnhaufer et al., Physiol. Plant, 61, pp. 555–558, 1984), differentiation of vessel elements (Iwasaki et al., Plant Cell Physiol., 32, pp. 1007–1014, 1991; Yamamoto et al., Plant Cell Physiol., 38, pp. 980–983, 1997), and cell extension (Azpiroz et al., Plant Cell, 10, pp. 219–230, 1998).

Furthermore, mechanisms and regulations of physiological actions of brassinosteroids have been being revealed by variety of studies on their biosynthesis (Clouse, Plant J. 10, pp. 1–8, 1996; Fujioka et al., Physiol. Plant, 100, pp. 710–715, 1997). At present, 40 or more brassinosteroids have been identified. Most of C28-brassinosteroids are common vegetable sterols, and they are considered to be biosynthesized from campesterol, which has the same carbon side chain as that of brassinolide.

Several Arabidopsis mutants which show characteristic dwarfism have been isolated, i.e., dwf1: Feldman et al., Science, 243, pp. 1351–1354, 1989; dim: Takahashi et al., Genes Dev., 9, pp. 97–107, 1995; and cbb1: Kauschmann et al., Plant J., 9, pp. 701–703, 1996. Their structural photomorphogenesis and dwarfism (cpd: Szekeres et al., Cell, 85, pp. 171–182, 1997) and de-etiolation (det2: Li et al., Science, 272, pp. 398–401, 1996; Fujioka et al., Plant Cell, 9, pp. 1951–1962, 1997) are known. The mutants have deficiencies in the brassinosteroid biosynthetic pathway. Furthermore, a dwarf mutant of Pisum sativum was recently characterized, and the mutant was reported as a brassinosteroid deficient mutant (Nomura et al., Plant Physiol., 113, pp. 31–37, 1997). In these plants, use of brassinolide is known to negate severe dwarfism of the mutants. Although these findings suggest that roles of brassinosteroids are indispensable for growth and development of plants, an effective tool other than the analysis of mutants has been desired to elucidate physiological importance of brassinolide.

As seen in researches of gibberellin action, specific inhibitors against the biosynthesis are generally very effective tools for elucidating physiological functions of endogenous substances. Specific inhibitors against brassinosteroid biosynthesis are expected to provide a new tool for understanding functions of brassinosteroids. Uniconazole is a potent plant growth regulator (PGR) which inhibits the oxidation employed by cytochrome P-450 in the steps of the gibberellin biosynthesis from ent-kaurene to ent-kaurenoic acid. Yokota et al. observed slight reduction of the amount of endogenous castasterone as a side effect of that compound (Yokota et al., "Gibberellin", Springer Verlag, New York, pp. 339–349, 1991). Although uniconazole in fact inhibits differentiation of vessel elements induced by brassinolide (Iwasaki et al., Plant Cell Physiol., 32, pp. 1007–1014, 1991), its inhibitory action against brassinolide is considered to be no more than an incidental action, because uniconazole essentially inhibits the gibberellin biosynthesis.

Several mutants deficient in biosynthetic enzymes are known for Arabidopsis, and their morphologic changes are unique to mutants with deficiency in the brassinosteroid biosynthesis. Therefore, the inventors of the present invention conducted intensive search for a compound inducing the morphologic changes unique to the mutants with the brassinosteroid biosynthesis deficiency to find a specific inhibitor against the brassinosteroid biosynthesis. As a result, they found that triazole compounds such as 4-(4-chlorophenyl)-2-phenyl-3-(1,2,4-triazoyl)butan-2-ol had the desired inhibitory action (Japanese Patent Unexamined Publication (Kokai) No. 2000–53657).

Regulation of flowering has been strongly desired from breeding and horticultural viewpoints, however, the regulation is still very difficult at present. Although there are several examples where flowering is regulated by application of a certain chemical agent in certain specific plant species, a general method has not been established. No successful regulation of flowering has been known in which regulation of biosynthesis/metabolism of plant hormones universally existing in plants is utilized.

DISCLOSURE OF THE INVENTION

The inventors of the present invention conducted various studies to regulate flowering of plants, and found that compounds that successfully regulate biosynthesis or metabolism of brassinosteroids as plant hormones are useful as flowering regulators. Thus, they achieved the present invention. In the aforementioned publications, it is described that compounds having an inhibitory action on brassinosteroids are useful as plant growth regulators, for example, for suppression of plant elongation, suppression of pollen growth, retention of freshness of flowers, use as anti-stress agents for plants, weeds control, suppression of plant retrogradation, hypertrophism of roots and the like. However, it is not suggested nor taught in the publications that such compounds have flowering regulatory action.

The present invention thus provides a flowering regulator which comprises a compound represented by the following formula (I):

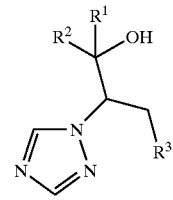

wherein $R^1$ represents a lower alkyl group, a lower alkenyl group, or a phenyl group which may be substituted, $R^2$ represents a lower alkyl group or a phenyl group which may be substituted, and $R^3$ represents a phenyl group which may be substituted, or a salt thereof.

According to preferred embodiments of the present invention, there are provided the aforementioned flowering regulator, wherein $R^1$ is a lower alkyl group, $R^2$ is a phenyl group which may be substituted with a halogen atom, and $R^3$ is 4-chlorophenyl group; and the aforementioned flowering regulator, which comprises 4-(4-chlorophenyl)-2-phenyl-3-(1,2,4-triazoyl)butan-2-ol.

According to further aspects of the present invention, there are provided use of a compound represented by the aforementioned formula (I) or a salt thereof for the manufacture of the aforementioned flowering regulator; and a method for regulating flowering, which comprises the step of applying an effective amount of the compound represented by the aforementioned formula (I) or a salt thereof to a plant.

The present invention provides a flowering accelerator composition, which comprises at least one compound which is represented by the following formula (I):

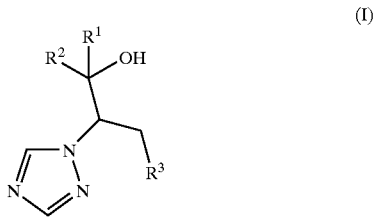

wherein $R^1$ represents a lower alkyl group, a lower alkenyl group, or a phenyl group which may be substituted, $R^2$ represents a lower alkyl group or a phenyl group which may be substituted, and $R^3$ represents a phenyl group which may be substituted, or a salt thereof, the composition being formulated with at least one ingredient including a diluent so that the composition can be applied to plants to accelerate flowering.

Moreover, the present invention provides a method of accelerating the flowering of a plant, wherein the method comprises treating the plant with at least one compound which is represented by the following formula (I):

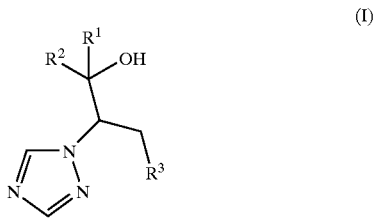

wherein $R^1$ represents a lower alkyl group, a lower alkenyl group, or a phenyl group which may be substituted, $R_2$ represents a lower alkyl group or a phenyl group which may be substituted, and $R^3$ represents a phenyl group which may be substituted, or a salt thereof, the treating including applying the compound to the plant to obtain flowering accelerating action.

BEST MODE FOR CARRYING OUT THE INVENTION

Figure 1:
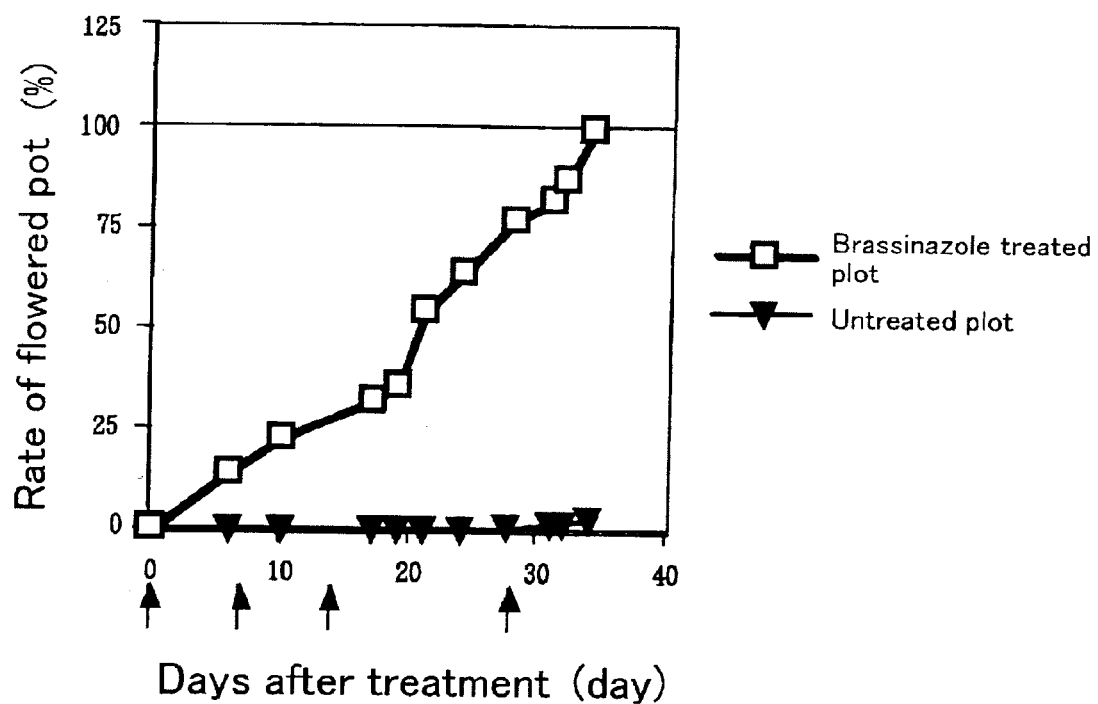
FIG. 1 shows action of the flowering regulator of the present invention. In the figure, □ indicates the result of a group treated with the flowering regulator of the present invention (brassinazole), and ▽ indicates the result of an untreated group. The vertical axis indicates a rate of flowering, and the horizontal axis indicates the number of days after the treatment. The arrows indicate the days when the flowering regulator is sprayed.

The entire disclosures of the specification of Japanese Patent Application No. 2000-226361 (filed on Jul. 27, 2000) are incorporated in the disclosures of the specification by reference.

In the aforementioned formula (I), $R^1$ represents a lower alkyl group, a lower alkenyl group, or a phenyl group which may be substituted. As the lower alkyl group, a linear or branched alkyl group having 1 to about 6 carbon atoms can be used. Examples include methyl group, ethyl group, n-propyl group, isopropyl group, n-butyl group, sec-butyl group, tert-butyl group, isobutyl group and the like. Among them, methyl group or ethyl group is preferred, and methyl group is particularly preferred. As the lower alkenyl group, a linear or branched alkenyl group having 2 to about 6 carbon atoms can be used. Examples include vinyl group, allyl group, 2-butenyl group and the like.

When the phenyl group represented by $R^1$ is substituted, types, numbers and substituting positions of substituents are not particularly limited. For example, the phenyl group may have preferably 1 to 3, more preferably 1 or 2 of substituents. Where the phenyl group has 2 or more substituents, they may be the same or different.

Examples of the substituent on the phenyl group include, for example, a halogen atom (any of fluorine atom, chlorine atom, bromine atom and iodine atom), a lower alkyl group (methyl group, ethyl group and the like), a lower cycloalkyl group (cyclopropyl group and the like), a halogenated lower alkyl group (trifluoromethyl group and the like), a lower alkoxy group (methoxy group, ethoxy group and the like), amino group, a mono- or dialkylamino group, carboxyl group, an alkoxycarbonyl group (ethoxycarbonyl group and the like), an alkanoyl group (acetyl group and the like), an aroyl group (benzoyl group and the like), an aralkyl group (benzyl group and the like), an aryl group (phenyl group and the like), a heteroaryl group (pyridyl group and the like), a heterocyclic group (pyrrolidinyl group and the like), hydroxyl group, nitro group, cyano group and the like. However, the substituents are not limited to these examples. Among them, a halogen atom, a lower alkyl group, a halogenated lower alkyl group, a lower alkoxy group and the like are preferred.

As $R^1$, methyl group, ethyl group, 2-propenyl group, and 2-pentenyl group are preferred, and methyl group is particularly preferred. As the lower alkyl group or the phenyl group which may be substituted represented by $R^2$ and the phenyl group which may be substituted represented by $R^3$, groups similar to each of those mentioned for the groups represented by $R^1$ can be used. $R^2$ is preferably an unsubstituted phenyl group, and 2,4-difluorophenyl group and the like may be used as a substituted phenyl group. Examples of the substituted phenyl group represented by $R^3$ include 4-chlorophenyl group and the like.

The compounds represented by the aforementioned formula (I) have two asymmetric carbon atoms in the fundamental structure, and may have one or more further asymmetric carbon atoms depending on the type of the substituent. Optically active compounds and diastereoisomers in pure forms based on the asymmetric carbon atoms as well as any mixtures of the isomers (for example, mixtures of two or more kinds of diastereoisomers), racemates and the like may be used as an active ingredient of the flowering regulator of the present invention. Furthermore, the compounds represented by the aforementioned formula (I) can form acid addition salts, and may further form acid addition salts depending on the type of the substituent. The types of the salts are not particularly limited, and examples of the salts include salts with mineral acids such as hydrochloric acid and sulfuric acid, salts with organic acids such as p-toluenesulfonic acid, methanesulfonic acid, and tartaric acid, metal salts such as sodium salts, potassium salts and calcium salts, ammonium salts, salts with organic amines such as triethylamine, salts with amino acids such as glycine and the like.

Specific examples of the compounds represented by the aforementioned formula (I) are described in Japanese Patent Unexamined Publication No. 2000-53657 and the specification of Japanese Patent Application No. 2000-57565, and any of the specific compounds described in these specifications can be used as an active ingredient of the flowering regulator of the present invention. The compounds represented by the aforementioned formula (I) can be easily prepared according to the methods described in Japanese Patent Unexamined Publication No. 2000-53657 and the specification of Japanese Patent Application No. 2000-57565.

The flowering regulator of the present invention which comprises the compound represented by the aforementioned formula (I) or a salt thereof as an active ingredient can be used as an agricultural and horticultural flowering regulator for the purpose of flowering regulation of plants. Although it is not intended to be bound by any specific theory, it is considered that the compounds represented by the aforementioned formula (I) have a specific inhibitory action against brassinosteroid biosynthesis, and exhibits flowering regulating action by inhibiting the biosynthesis of brassinosteroids which universally exist in plants. Therefore, plants to which the flowering regulator of the present invention can be applied are not particularly limited, and the flowering regulator of the present invention may be applied to any plant including crops such as rice and fruit, garden plants such as tulip and rose and the like.

The term "flowering regulation" or its synonyms used in the present specification should be construed in their broadest sense including, for example, regulation of day of flowering, hour of flowering and the like, flowering accelerating action and the like, and should not be construed in any limitative way. For example, delivery of horticultural plants can be easily planned by regulating day of flowering, and costs for market input can be reduced. Furthermore, new varieties of fruit trees are generally grown by mating, and several years are usually required before flowering. The period of time before flowering can be shortened to about several months by using the flowering regulator of the present invention, and hence it becomes easy to create new varieties. Furthermore, in cultivation of rice, apples or the like, harvest season can be hastened by advancing day of flowering, and thus damages by typhoons can be avoided.

The flowering regulator of the present invention can be formulated as an agricultural and horticultural composition, for example, by using formulation additives well known in the art. Forms of the agricultural and horticultural composition are not particularly limited, and any forms that can be used in the art may be chosen. For example, compositions in the forms of emulsions, liquids, oils, water soluble powders, wettable powders, flowables, powders, subtilized granules, granules, aerosols, fumigants, pastes and the like can be used. The methods for manufacturing the agricultural and horticultural composition are also not particularly limited, and any methods available to those skilled in the art can be appropriately employed. As the active ingredient of the flowering regulator of the present invention, two or more of the compounds represented by the aforementioned formula (I) or salts thereof may be used in combination. Furthermore, other active ingredients of agricultural and horticultural chemicals such as insecticides, fungicides, insecticidal and fungicidal agents, herbicides and the like may be formulated. Methods of application and doses of the flowering regulator of the present invention can be suitably chosen by those skilled in the art depending on conditions including a purpose of application, a dosage form, a plot to be treated and the like, and are easily chosen by referring to the following example.

EXAMPLES

The present invention will be explained more specifically with reference to an example. However, the scope of the present invention is not limited to the following example.

Example 1

Forty four pots of American Blue (*Evolvulus pilosus*) of about one month after cutting, which were purchased as-commercial products, were grown in a greenhouse at 22° C. under a natural light condition during the day and an artificial light condition during the night. These pots were divided into two groups, and 22 plants were sprayed with brassinazole [4-(4-chlorophenyl)-2-phenyl-3-(1,2,4-triazoyl)butan-2-ol] solution in an amount of 1000 g/ha on days 0, 7, 14 and 30. The other group (22 plants) was grown under the same conditions except for the treatment with the agent. As the brassinazole solution, 0.5 mg/ml aqueous solution containing 0.1% dimethyl sulfoxide and 0.1% Tween 20 was prepared, and diluted to a 1/10 concentration with water upon use and sprayed by using a spray in the predetermined amount.

In the brassinazole treated plot, a phenomenon that flowering occurred after flower-bud formation was observed. Whilst, flowering significantly delayed in the untreated plot under the aforementioned cultivation conditions, and flowering was observed on only one plant on day 35. Thus, the flowering accelerating effect of brassinazole was clearly demonstrated.

INDUSTRIAL APPLICABILITY

The flowering regulator of the present invention is useful because it enables regulation of flowering of agricultural and horticultural plants to allow successful regulation of harvest or delivery time.

What is claimed is:

1. A method of accelerating the flowering of a plant, wherein the method comprises treating the plant with at least one compound which is represented by the following formula (I):

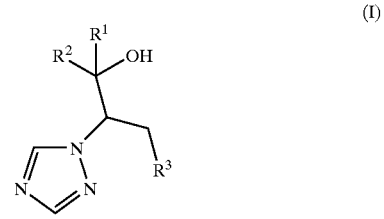

wherein $R^1$ represents a lower alkyl group, a lower alkenyl group, or a phenyl group which may be substituted, $R^2$ represents a lower alkyl group or a phenyl group which may be substituted, and $R^3$ represents a phenyl group which may be substituted, or a salt thereof, the treating including applying the compound to the plant to obtain flowering accelerating action.

2. The method of claim 1, wherein $R^1$ is a lower alkyl group, $R^2$ is a phenyl group which may be substituted with a halogen atom, and $R^3$ is a 4-chlorophenyl group.

3. The method of claim 1, wherein the at least one compound comprises 4-(4-chlorophenyl)-2-phenyl-3-(1,2,4-triazol)butan-2-ol.

4. The method of claim 1, wherein the method comprises treating the plant with a composition which comprises at least one compound of formula (I).

5. The method of claim 4, wherein the composition further comprises water.

6. The method of claim 4, wherein the composition comprises an aqueous solution.

7. The method of claim 5, wherein the method comprises applying the composition at least onto leaves of the plant.

8. The method of claim 4, wherein the method comprises spraying the composition onto the plant.